United States Patent [19]
Takeuchi et al.

[11] Patent Number: 5,190,039
[45] Date of Patent: Mar. 2, 1993

[54] APPARATUS AND METHOD FOR MONITORING BODY ORGANS

[75] Inventors: Hiroshi Takeuchi, Matsudo; Fumio Kawaguchi, Tokyo; Yuichi Yamashita, Hachioji; Kazuo Takeda, Kokubunji; Yoshitoshi Ito, Ome; Yasuhiro Mitsui, Fuchu; Keiichi Nagai, Higashiyamato, all of Japan

[73] Assignee: Hitachi, Ltd., Tokyo, Japan

[21] Appl. No.: 622,607

[22] Filed: Dec. 5, 1990

[30] Foreign Application Priority Data

Dec. 8, 1989 [JP] Japan .................. 1-317781

[51] Int. Cl.⁵ .............................................. A61B 5/00
[52] U.S. Cl. ...................... 128/633; 128/666
[58] Field of Search ............... 128/633, 634, 635, 664, 128/665, 666

[56] References Cited

U.S. PATENT DOCUMENTS

| | | | |
|---|---|---|---|
| 4,281,645 | 8/1981 | Jobsis | 128/633 |
| 4,338,174 | 7/1982 | Tamura | 128/635 |
| 4,476,870 | 10/1984 | Peterson | 128/665 |
| 4,664,119 | 5/1987 | Bessman | 128/635 |
| 4,741,343 | 5/1988 | Bowman | 128/635 |
| 5,066,859 | 11/1991 | Karkar et al. | 128/633 |

OTHER PUBLICATIONS

*Respiratory Physiology*, Mines, Allan H. pp. 62-63 ©1981 Raven Press New York.
*Medical Physiology*, Brown, et al, ed., ©1983 John Wiley and Sons, New York, pp. 354-360.
*Japanese Journal of Magnetic Resonance in Medicine*, "Localized MRS Studies of Exercising Limbs and Simultaneous Evaluation of Oxygen Delivery to Tissue", B. Chance, et al., vol. 8, Supplement-2, 1988.

Primary Examiner—Lee S. Cohen
Assistant Examiner—Robert L. Nasser
Attorney, Agent, or Firm—Antonelli, Terry Stout & Kraus

[57] ABSTRACT

An apparatus and a method for non-invasively measuring oxygen partial pressure in a living body in which light is thrown on a living body to be measured, the oxygen saturation of the living body is obtained from the light absorption spectrum or light scattering spectrum thereof, the temperature and/or pH of the living body is obtained from a nuclear magnetic resonance signal from the living body, and the oxygen partial pressure in the living body, useful for the diagnosis thereof, is determined on the basis of not only the oxygen saturation but also the temperature and/or pH of the living body.

17 Claims, 3 Drawing Sheets

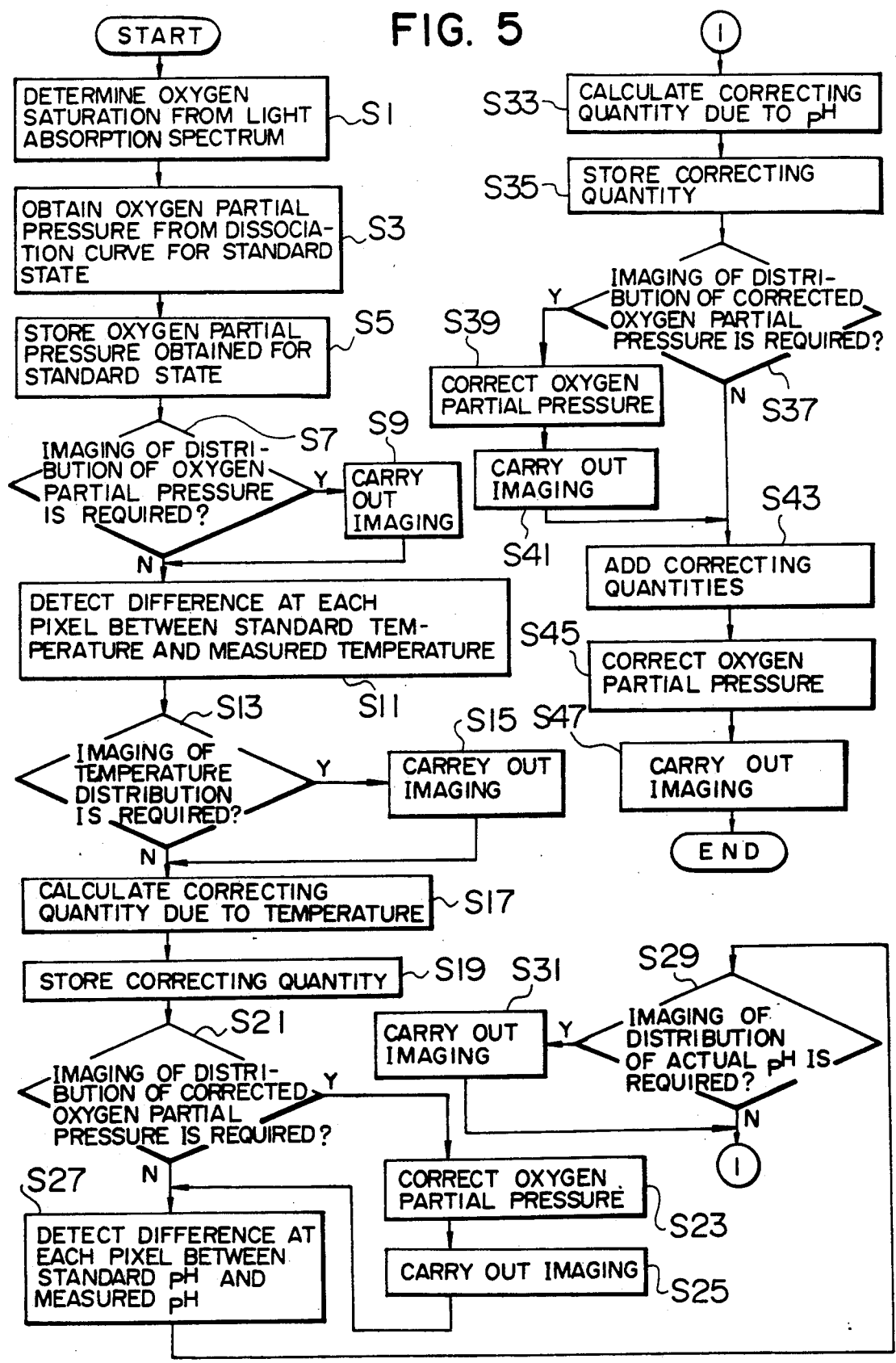

APPARATUS AND METHOD FOR MONITORING BODY ORGANS

BACKGROUND OF THE INVENTION

The present invention relates to an apparatus and a method for monitoring body organs, and more particularly to an apparatus and a method for measuring the oxygen content of a body organ (that is, oxygen partial pressure in the body organ) non-invasively.

In a living body, there is always carried out a process that adenosine triphosphate (ATP) serving as an energy source is produced by consuming oxygen and glucose. Accordingly, in order to diagnose the metabolic state of the living body, it is very important to know how oxygen and glucose are distributed in the living body, non-invasively. Recently, various methods of measuring the oxygen content of a living body optically have been tried, and a part of the methods has been put in practical use. The above methods utilize a fact that the optical characteristics of hemoglobin included in a red blood cell for carrying oxygen to the whole of a living body, the optical characteristics of cytochrome playing an important role in a process for producing adenosine triphosphate in the mitchondrion included in a cell, and the optical characteristics of myoglobin for storing oxygen in a muscle, vary depending upon the state of oxidation, that is, their optical characteristics at the oxygenated state are different from those at the deoxygenated state. Specifically, a method of determining the oxygen content from a change in light absorption spectrum is most frequently used. According to this method, as disclosed in U.S. Pat. No. 4,281,645 in detail, light is introduced into a living body, the light absorption coefficient of an oxygen content indicator substance which is to be examined, is measured, the oxygen saturation of the indicator substance (that is, how much oxygen is introduced into the indicator substance) is determined from the light absorption coefficient of the indicator substance, an oxygen content is determined from the oxygen saturation on the basis of a predetermined relation between the oxygen content and the oxygen saturation. That is, the oxygen partial pressure in the living body can be determined. In the greater part of conventional methods, the oxygen partial pressure is determined on the basis of the above principle. Recently, the imaging of the distribution of oxygen partial pressure has been tried (refer to, for example, Proc Natl Acad Sci U.S.A., Vol. 85, Jul., 1988, pages 4971 to 4975).

However, a curve indicating the relation between the oxygen saturation and the oxygen partial pressure (that is, oxygen dissociation curve) is shifted, depending upon the acidity (pH) and temperature T of a portion to be examined. Accordingly, the oxygen partial pressure determined only from the oxygen saturation data (which is obtained from the light absorption coefficient) does not indicate a correct oxygen partial pressure, but contains an error. When the above oxygen partial pressure is used for diagnosing whether a living body is normal or abnormal, the diagnosis may be erroneous.

As mentioned above, the conventional technology does not take into consideration the shift of oxygen dissociation curve due to the acidity (pH) and temperature of that portion of a person which is to be examined. Thus, the conventional technology cannot determine a correct oxygen partial pressure nor image the distribution of correct oxygen partial pressure.

SUMMARY OF THE INVENTION

It is a first object of the present invention to provide an apparatus for and a method of measuring an oxygen partial pressure in a living body non-invasively and correctly.

It is a second object of the present invention to display information for obtaining the correct oxygen partial pressure in the form of a picture image.

In order to attain the first object, according to the present invention, light is incident on a living body to be measured, the oxygen saturation of the living body is determined from the light absorption spectrum or light scattering spectrum of the living body, the temperature and/or acidity of the living body is determined from a nuclear magnetic resonance signal obtained from the living body, and the oxygen partial pressure in the living body is correctly determined from a relation among the oxygen partial pressure, the oxygen saturation, and the temperature and/or acidity.

Now, a case where the oxygen partial pressure is determined from the light absorption spectrum of hemoglobin, will be explained in more detail, by way of example.

The light absorption spectrum of hemoglobin changes, depending upon the degree of oxidation of hemoglobin. In FIG. 2, a curve 31 indicates the absorption spectrum of oxygenated hemoglobin, and a curve 32 indicates the absorption spectrum of deoxygenated hemoglobin. Thus, it seems that the degree of oxidation of hemoglobin can be determined from the difference at a specified wavelength between a measured absorption curve and the curve 31 or 32. However, it is very difficult to detect the above difference, because the living body scatters light in a great degree. When a wavelength, at which the absorption coefficient of oxygenated hemoglobin is equal to that of deoxygenated hemoglobin (for example, a wavelength of 810 nm shown in FIG. 2 for indicating an isobestic point) is used as a reference wavelength, and a measuring wavelength which is different from the reference wavelength but can neglect the difference in light scattering between the reference wavelength and the measuring wavelength, for example, a measuring wavelength of 770 nm is used, the adverse effect of the light scattering of the living body on the detection of the difference between the light absorption coefficients can be eliminated, and the oxygen saturation can be accurately determined.

However, the oxygen dissociation curve is shifted depending upon the acidity (for example, pH) of a portion to be examined. FIG. 3 shows examples of the shifting of the oxygen dissociation curve due to pH. In FIG. 3, reference numeral 41 designates a dissociation curve for pH = 7.4, 42 a dissociation curve for pH = 7.6, and 43 a dissociation curve for pH = 7.2. Similarly, the oxygen dissociation curve is shifted, depending upon the temperature of the to-be-examined portion. Accordingly, when the pH and temperature of the to-be-examined portion are not known, it is impossible to determine the oxygen partial pressure.

When means for measuring nuclear magnetic resonance characteristics is added to an optical apparatus for executing the above optical method, the pH of a desired portion can be determined from the chemical shift of $^{31}P$ in an inorganic phosphate (refer to a Japanese publication "Byotai Seiri (Sick Body Physilogy)" Vol. 4, No. 2, 1985, pages 104 to 110). This is because the relation between the pH and the chemical shift of $^{31}$P in the inorganic phosphate is given by a curve 51 shown in FIG. 4. It is to be noted that values of chemical shift in FIG. 4 are determined by using a peak value in creating phosphate as a reference.

Further, the temperature of a desired portion can be determined by measuring the longitudinal relaxation time T$_1$ of the magnetic resonance of $^1$H (refer to Medical Physics, Vol. 10, No. 3, May/Jun., 1983). This is because the longitudinal relaxation time T$_1$ in various portions of a living body is a function of the temperature of the portions. As mentioned above, when the means for measuring nuclear magnetic resonance characteristics is added to the optical apparatus, the pH and temperature of a desired portion can be measured non-invasively at the same time as information on light absorption at the above portion is obtained, and an oxygen dissociation curve is univocally determined on the basis of the measured values of pH and temperature. Thus, the oxygen partial pressure in the desired portion can be correctly determined. The distribution of the chemical shift of $^{31}$P and the distribution of the longitudinal relaxation time of $^1$H can be displayed in the form of a tomogram. Accordingly, in a case where the distribution of light absorption information can be obtained, the light absorption information at each pixel can be corrected on the basis of the above chemical shift and longitudinal relaxation time at the pixel, and thus it is possible to display the distribution of a correct oxygen partial pressure.

It is very important to the diagnosis of a living body to measure the oxygen partial pressure in the living body correctly, as will be explained below. The oxygen saturation corresponding to a measured state of the living body is usually more than 80%, and lies in the saturation region of the oxygen dissociation curve. That is, a change in oxygen saturation due to a slight change of the state of the living body is too small to be detected. On the other hand, the oxygen partial pressure in this case is not put in a saturation state, but can surely detect the slight change of the stage of the living body. Thus, by measuring the oxygen partial pressure correctly, the state of the living body can be exactly diagnosed.

Further, by displaying the distribution of correct oxygen partial pressure in the living body as a picture image, the diagnosis of the living body can be made rapidly and exactly.

BRIEF DESCRIPTION OF THE DRAWINGS

FIG. 5 is a flow chart showing the operation of the embodiment of FIG. 1.

DESCRIPTION OF THE PREFERRED EMBODIMENTS

Now, embodiment of the present invention will be explained, with reference to the drawings.

Figure 1:
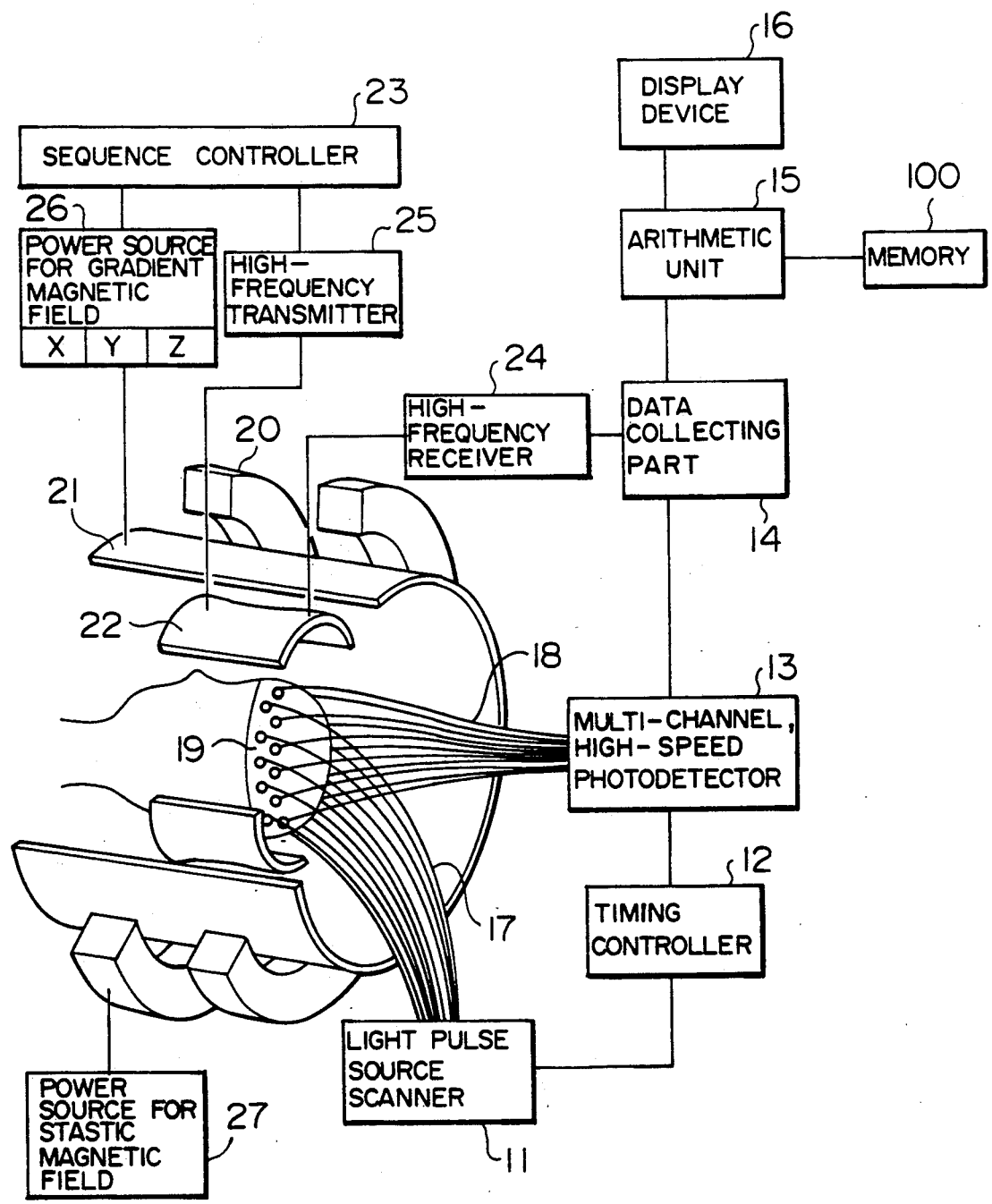
FIG. 1 is a diagram, partly in block and partly schematic, of an embodiment of an apparatus for measuring a living body in accordance with the present invention.
Figure 2:
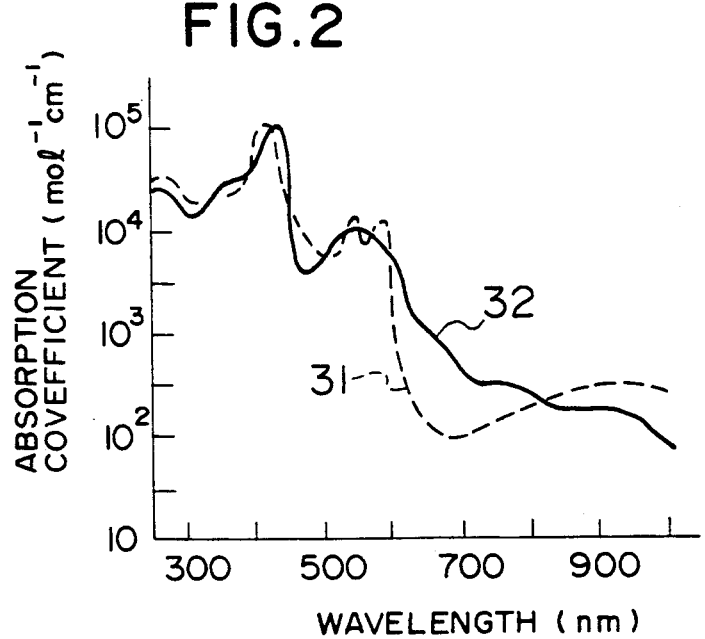
FIG. 2 is a graph showing light absorption spectra of oxygenated hemoglobin and deoxygenated hemoglobin.
Figure 3:
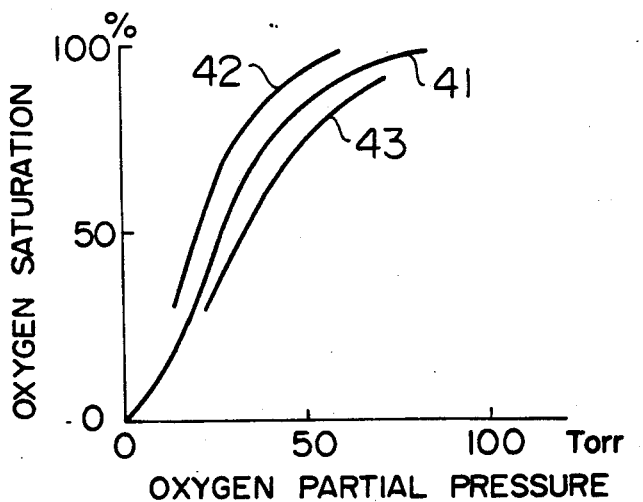
FIG. 3 is a graph showing oxygen dissociation curves of hemoglobin.
Figure 4:
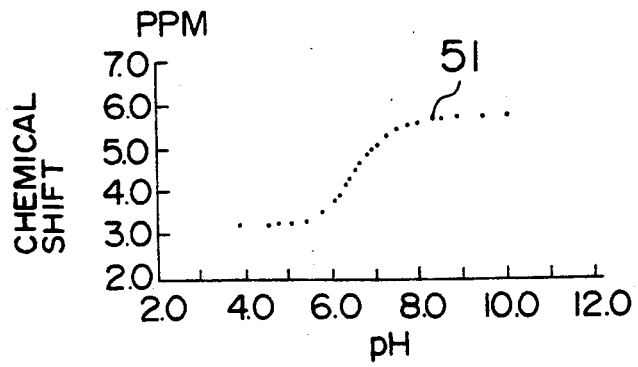
FIG. 4 is a graph showing a relation between the chemical shift of $^{31}$P in an inorganic phosphate and acidity pH.

FIG. 1 is a diagram showing an embodiment of an apparatus for measuring a living body in accordance with the present invention. First, explanation will be made of a method of measuring the oxygen saturation of homoglobin optically and displaying the distribution of oxygen saturation as a picture image. In order to obviate the adverse effect of the violent light scattering due to a living body, a light pulse source 11 is used. A measuring wavelength is selected so that the absorption spectrum of oxygenated hemoglobin at this wavelength is greatly different from the absorption spectrum of deoxygenated hemoglobin at the wavelength. In order to remove information other than light absorption, data at a reference wavelength, at which the light absorption coefficient of oxygenated hemoglobin is equal to that of deoxygenated hemoglobin, is used as reference data. Further, in order to identify an optical path for obtaining a light absorption coefficient, output light is measured in such a manner that a time gate is set on the output of a photo-detector 13. Light traveling in a living body is greatly attenuated by scattering. For example, light traveling in the head of an adult is attenuated to one ten-billionth of an initial value. Accordingly, not only a high-sensitivity detector is required, but also it is required to introduce light efficiently into the living body and to take out transmitted light efficiently. In the present embodiment, two bundles 17 and 18 of optical fibers are attached to a cap-shaped optical coupler 19 which is put in close contact with the head, to introduce light efficiently into the head and to take out output light efficiently. A plurality of input fibers 17 and a plurality of output fibers 18 are arranged around the head. A pulsed laser beam is introduced into one of the input fibers 17, and output light is detected by the all the output fibers 18 and a multi-channel, high-speed photo-detector 13 under control of a timing controller 12. At this time, the time response of output light is measured by the photodetector 13, and a time gate is used, if necessary, to obtain a desirable signal. The above operation is performed for all of the input fibers 17. Thus, light absorption information in the whole region of the head is obtained. The above information is sent to an arithmetic unit 15 through a data collecting part 14, to display a tomogram indicative of the distribution of light absorption values by a display device 16.

The distribution of oxygen saturation of hemoglobin can be obtained by the above-mentioned optical measurement. However, the oxygen dissociation curve indicative of the relation between the oxygen saturation and the oxygen partial pressure is shifted depending upon the pH and temperature of the living body. Accordingly, it is impossible to obtain a clinically significant oxygen partial pressure only from the oxygen saturation of hemoglobin. In the present embodiment, in order to correct the shifting of the oxygen dissociation curve due to the pH and temperature of the living body, a nuclear magnetic resonance measuring apparatus is added to an optical measuring apparatus, as shown in FIG. 1. In FIG. 1, reference numeral 20 designate a coil for applying a static magnetic field to a person to be examined, 21 a coil for generating a gradient magnetic field necessary for imaging, and 22 a probe for applying a high-frequency magnetic field to the to-be-inspected person and receiving a signal therefrom.

Of information obtained by nuclear magnetic resonance, the relaxation phenomenon of magnetic resonance of $^1$H (namely, proton) is first discussed. The above relaxation phenomenon occurs in the following manner. When protons which are put in a static magnetic field in a thermal equilibrium state and have the same magnetization direction, are applied with a high-frequency magnetic field having a resonance frequency (namely, Larmor frequency) $\omega_o$, the protons absorb the high-frequency energy, and the magnetization is inclined toward the direction of the high-frequency magnetic field. When the high-frequency magnetic field is removed, the protons give off energy, and the magnetization is returned to an initial state at a time the high-frequency magnetic field is not yet applied. For example, let us consider a case where the direction of the magnetization in a thermal equilibrium state is parallel to a Z-direction. When a high-frequency magnetic field having the Larmor frequency $\omega_o$ is applied for a predetermined time so that the direction of magnetization is rotated through an angle of 180°, the magnetization is oriented in a direction opposite to the Z-direction, and then the absolute value of the negative value of the Z-component of the magnetization decreases with time. Thus, the magnetization is finally returned to the initial state in the thermal equilibrium state. At this time, the time variation of Z-component of the magnetization is given by the following equation:

$$M(t) = M_0 \left\{ 1 - 2\exp\left(-\frac{t}{T_1}\right) \right\} \quad (1)$$

where a time constant $T_1$ is called "longitudinal relaxation time", and is given by the following equation:

$$1/T_1 = \frac{3\gamma^4 h^2}{10\gamma^6} \left( \frac{\tau_c}{1 + \omega_o^2 \tau_c^2} + \frac{4\tau_c}{1 + 4\omega_o^2 \tau_c^2} \right) \quad (2)$$

In the equation (2), h is equal to $h/2\pi$ (whereh indicates Planck's constant), $\gamma$ is the gyromagnetic ratio of proton ($^1$H) $\omega_o$ indicates a Larmon frequency, $\tau_c$ is equal to $\tau_c^\circ$ exp (Ea/kT). Ea indicates the excitation energy of molecular motion, k is Boltzmann's constant, and T indicates an absolute temperature.

As described above, the longitudinal relaxation time $T_1$ is a function of a variable $\tau_c$, which is a function of temperature. That is, the relaxation time $T_1$ is a function of temperature. Accordingly, the temperature can be determined by measuring the relaxation time $T_1$. For example, in a case where a static magnetic field of 0.15 T (tesla) is used, the longitudinal relaxation time for the white matter of a brain and that for the grey matter thereof are 300 ms and 475 ms, respectively.

It has been already known that, like the distribution density of proton and the transverse relaxation time $T_2$ thereof, the longitudinal relaxation time $T_1$ which is one of fundamental parameters of magnetic resonance of proton, can be displayed as a picture image. When a pulse sequence including a high-frequency magnetic field pulse and the parameters with respect to the pulse sequence are varied by a sequence controller 23, and simultaneous equations with respect to data obtained from a high-frequency receiver 24 and the data collecting part 14 are solved, a picture image indicative of the distribution of measured values of $T_1$ can be obtained. The standard distribution of $T_1$ in a brain has been known. Accordingly, the temperature of the brain can be estimated from the deviation of the measured value of $T_1$ from the standard value thereof.

In the above, explanation has been made of a method of obtaining the temperature information on a living body necessary for determining the oxygen partial pressure, by utilizing nuclear magnetic resonance. Next, explanation will be made of a method of obtaining the acidity information on the living body by utilizing nuclear magnetic resonance. Although the hydrogen exponent (namely, pH) is usually used for indicating acidity, the hydrogen ion concentration may be used, as it is.

Other information than the relaxation phenomenon (for example, spectroscopy) is also obtained by nuclear magnetic resonance. The spectroscopy is based upon a phenomenon that the resonance frequency of a nuclide in a living body is slightly shifted by environment. This shift is called "chemical shift". Specifically, the chemical shift of $^{31}$P is closely related to the metabolic function of a living body. Since the measurement of the chemical shift of $^{31}$P is relatively easy, this chemical shift has been investigated in detail. For example, it has been known that the resonance frequency of $^{31}$P in an inorganic phosphate varies with a pH value.

The basic method of detecting the chemical shift is as follows. A 90° RF pulse (namely, high-frequency magnetic field pulse for rotating the direction of magnetization through an angle of 90°) is supplied from a high-frequency transmitter 25 to a probe 22, and then spectral analysis is carried out for the FID (free induction decay) signal received by the probe 22, to determine the chemical shift. In local spectroscopy for examining only a limited portion, a portion to be examined is limited by selective excitation techniques (namely, slicing techniques) based upon a combination of a gradient magnetic field and a selective pulse containing a limited number of frequency components, or surface coil techniques, and the FID signal is measured. Further, imaging techniques have been developed. For example, a slice which is perpendicular to, for example, a Z-direction, is selected by the slicing techniques, the time duration or space gradient of each of an X-gradient field and a Y-gradient field is stepwise changed with the same increment or decrement by means of a power source 26 for gradient magnetic field and a coil 21 for gradient magnetic field, to measure the FID signal a plurality of times, and the three-dimensional data thus obtained is subjected to Fourier transform to make possible spectroscopic imaging. Accordingly, the distribution of pH can be obtained from the distribution of chemical shift of $^{31}$P.

Next, explanation will be made of a method of determining an oxygen partial pressure correctly from the oxygen saturation obtained from a light absorption spectrum, by correcting the shift of oxygen dissociation curve on the basis of the temperature and acidity information thus obtained, with reference to FIG. 5. In a memory 100 shown in FIG. 5, data on the oxygen dissociation curve in a standard state (for example, a state having a pH value of 7.0 and a temperature of 36.5° C.) are tabulated. Further, the memory 100 stores therein data on the degree of shifting of the dissociation curve due to the difference between a standard temperature and the measured temperature of the living body, and data on the degree of shifting of the dissociation curve due to the difference between a standard pH-value and a measured pH-value.

Referring now to FIG. 5, oxygen saturation is detected from a light absorption spectrum (step 1). The oxygen saturation thus obtained is compared with data on a standard dissociation curve to obtain an oxygen partial pressure based upon the assumption that the whole of a living body is put in a standard state (step 3). The oxygen partial pressure thus obtained is stored in the memory (step 5). This oxygen partial pressure is obtained at each pixel, through an error is contained therein. The distribution of the oxygen partial pressure is imaged, if necessary (steps 7 and 9). In step 11, the longitudinal relaxation time $T_1$ in that portion of the living body where the light absorption spectrum of the step 1 has been obtained, is measured by a nuclear magnetic resonance apparatus, and the difference between an actual temperature of the above portion and a standard temperature is determined from the difference between the measured relaxation time $T_1$ and a relaxation time $T_{1S}$ in the standard state. Since the actual temperature of the portion can be obtained by adding the above temperature difference to the standard temperature, the temperature distribution in the portion is imaged, if necessary (steps 13 and 15).

In step 17, the shifting quantity of the dissociation curve is determined from data on the shifting of the dissociation curve due to temperature which data is stored in the memory 100, on the basis of the temperature difference obtained in the step 11, that is, a correcting quantity for the oxygen partial pressure due to temperature is determined. This correcting quantity is given by a vector quantity on a plane containing the dissociation curve, and has both a magnitude and a direction. The correcting quantity is stored in the memory 100 (step 19). When information on the oxygen partial pressure which has been subjected to temperature correction, is required in step 21, the oxygen partial pressure which has been obtained for the standard state is read out from the memory 100 pixel by pixel, and the above correcting quantity is added to the read-out oxygen partial pressure to obtain the oxygen partial pressure having been subjected to temperature correction (step 23). The distribution of the corrected oxygen partial pressure thus obtained is imaged (step 25).

In step 27, the chemical shift in that portion of the living body where the light absorption spectrum of the step 1 has been obtained, is measured by the nuclear magnetic resonance apparatus, and the difference between the actual pH of the above portion and the standard pH thereof is determined from the measured chemical shift and the standard chemical shift. The distribution of actual pH which is obtained from the measured chemical shift, is imaged, if necessary (steps 29 and 31).

In step 33, the shifting quantity of the dissociation curve is determined from data on the shifting of the dissociation curve due to pH which data is stored in the memory 100, on the basis of the pH difference obtained in the step 27, that is, a correcting quantity for the oxygen partial pressure due to pH is determined. Like the correcting quantity due to temperature, the correcting quantity due to pH is given by a vector quantity on a plane containing the dissociation curve. The correcting quantity due to pH is also stored in the memory 100 (step 35).

When information on the oxygen partial pressure which has been subjected to pH correction, is required in step 37, the oxygen partial pressure which has been obtained for the standard state, is read out from the memory 100 pixel by pixel, and the correcting quantity due to pH is added to the read-out oxygen partial pressure to obtain the oxygen partial pressure having been subjected to pH correction (step 39). The distribution of the corrected oxygen partial pressure thus obtained is imaged (step 41).

In step 43, the correcting quantity due to temperature and the correcting quantity due to pH are both read out from the memory 100, and are added to obtain a resultant correcting quantity. In step 45, the oxygen partial pressure obtained for the standard state is read out from the memory 100, and the resultant correcting quantity is added to the read-out oxygen partial pressure to obtain the oxygen partial pressure having been subjected to both temperature correction and pH correction. The distribution of the oxygen partial pressure thus corrected is imaged (step 47).

In the present embodiment, an oxygen partial pressure for a standard state is obtained from a light absorption spectrum and the oxygen dissociation curve for the standard state, and then the above oxygen partial pressure is subjected to temperature correction and pH correction to obtain a correct oxygen partial pressure. Alternatively, the correct oxygen partial pressure may be calculated directly from the oxygen saturation which is obtained from the light absorption spectrum, and the temperature and/or pH of a living body which is obtained from a nuclear magnetic resonance signal.

Further, in the present embodiment, the distribution of oxygen partial pressure is outputted in the form of a picture image. Alternatively, the distribution of oxygen partial pressure may be outputted in the form of a graph or table. Furthermore, picture images obtained in two or more of the steps 9, 15, 25, 31, 41 and 47 may be simultaneously displayed on a single display screen.

In the present invention, there is shown a case where the distribution of oxygen is determined from information on the light absorption of red blood cells or hemoglobin. It has been known that scattered light, also, contains information on the oxidation of hemoglobin. Information on scattered light can be obtained by analyzing the time response of a signal measured by the multi-channel, high-speed photodetector of FIG. 1. In a case where the oxygen partial pressure is detected from the scattering image thus obtained, also, a correct oxygen partial pressure can be determined on the basis of the temperature correction and pH correction which are carried out by the apparatus of FIG. 1.

In the present embodiment, the oxygen partial pressure in a living body is estimated from the optical property of hemoglobin. Alternatively, the oxygen partial pressure may be estimated from the optical property of myoglobin in musculature or cytochrome in a cell. In this case, also, the oxygen dissociation curve of myoglobin or cytochrome is affected by temperature and pH, and the temperature correction and pH correction are required to obtain a correct oxygen partial pressure.

As mentioned above, in the present invention, nuclear magnettic resonance characteristics of a slice are measured together with optical characteristics of the slice, and measured values thus obtained are used to image the distribution of correct oxygen partial pressure. Further, in the present embodiment, the distribution of at least two of oxygen partial pressure, temperature and acidity can be displayed on the same display screen.

Referring again to FIG. 1, the optical fibers 17 and 18 and the optical coupler 19 are made of a material which will hardly disturb the uniformity of the static magnetic field generated by a power source 27 and the coil 20, and whose optical characteristics are hardly affected by a strong magnetic field. Further, means for compensating for a change in optical properties of the optical fiber and the optical coupler due to the strong magnetic field may be additionally provided, if necessary. Thus, the measuring accuracy can be improved to a desired level.

According to the above-mentioned, living-body measuring apparatus of the present invention, the distribution of oxygen partial pressure can be exactly imaged in a non-invasive manner. Accordingly, it is possible to early detect, for example, a disease of the brain due to a reduction in oxygen partial pressure within the brain, and the early diagnosis of a reduction in function of the brain and the aging thereof is made possible. Further, the living-body measuring apparatus is non-invasive, and hence can carry out the diagnosis repeatedly to observe the effect of medication for the above disease. It is impossible for a conventional diagnostic instrument to make such repeated diagnosis. Accordingly, the present invention will exhibit a remarkable effect on an aging society.

We claim:

1. A living-body measuring apparatus for measuring the oxygen partial pressure in a living body non-invasively, comprising:
   means for throwing light on a living body;
   means for detecting light having passed through the living body;
   means for obtaining the oxygen saturation of an oxygen content indicator substance at a predetermined portion of the living body, from the detected light;
   means for generating nuclear magnetic resonance in the living body, to obtain the temperature of the predetermined portion from a first resonance characteristic of the nuclear magnetic resonance;
   means for generating nuclear magnetic resonance in the living body, to obtain the acidity of the predetermined portion from a second resonance characteristic of the nuclear magnetic resonance;
   means for determining an oxygen partial pressure from the oxygen saturation in accordance with an oxygen dissociation curve of the oxygen content indicator which is compensated with the temperature and the acidity; and
   means for displaying the oxygen partial pressure.

2. A living-body measuring apparatus according to claim 1, wherein the means for throwing light on the living body includes a light pulse source, a plurality of first optical couplers adapted to be put in close contact with the living body, and a plurality of first optical fibers connected between the light pulse source and the first optical couplers.

3. A living-body measuring apparatus according to claim 2, wherein the light detection means includes a plurality of second optical couplers adapted to be put in close contact with the living body, a multi-channel, high-speed photodetector, and a plurality of second optical fibers connected between the photodetector and the second optical couplers.

4. A living-body measuring apparatus according to claim 3, wherein said light throwing means and said light detection means are made of a material which makes negligibly small a disturbance in a magnetic field used for obtaining the temperature and acidity of the predetermined portion.

5. A living-body measuring apparatus according to claim 3, wherein in a case where the head of the living body is measured, the first and second optical couplers are attached to a cap adapted to be put in close contact with the head, at positions on the substantially same plane as a slice used in nuclear magnetic resonance measurement for obtaining the temperature and the acidity.

6. A living-body measuring apparatus according to claim 1, wherein said light detection means detects said light after said light has passed through said living-body and been subjected to one of absorption and scattering due to one of a red blood cell and hemoglobin in said living-body.

7. A living-body measuring apparatus according to claim 1, wherein said light detection means detects said light after said light has passed through said living-body and been subjected to one of absorption and scattering due to one of cytochrome and myoglobin in said living-body.

8. A living-body measuring apparatus according to claim 1, wherein the means for obtaining the oxygen saturation determines the oxygen saturation from a light spectrum obtained by the light detection means.

9. A living-body measuring apparatus according to claim 1, wherein said means for generating nuclear magnetic resonance to obtain the temperature of the predetermined portion obtains the temperature of the predetermined portion by determining a longitudinal relaxation time of a first nuclide in the living body.

10. A living-body measuring apparatus to claim 9, wherein said means for generating nuclear magnetic resonance to obtain the temperature of the predetermined portion obtains the temperature of the predetermined portion by determining a longitudinal relaxation time of $^1H$ in the living body.

11. A living-body measuring apparatus according to claim 9, wherein said means for generating nuclear magnetic resonance to obtain the acidity of the predetermined portion obtains the acidity of the predetermined portion by determining a chemical shift of a second nuclide in the living body.

12. A living-body measuring apparatus for measuring the oxygen partial pressure distribution in a slice of a living body non-invasively, comprising:
   means for throwing light on a living body;
   means for detecting light having passes through the slice of the living body;
   means for obtaining the oxygen saturation of an oxygen content indicator substance in the sliced of the living body, from the detected light;
   means for generating nuclear magnetic resonance in the slice of the living body, to obtain the temperature distribution in the slice from a first resonance characteristic of the nuclear magnetic resonance;
   means for generating nuclear magnetic resonance in the slice of the living body, to obtain the acidity distribution in the slice from a second resonance characteristic of the nuclear magnetic resonance;
   means for converting said oxygen saturation distribution into a oxygen partial pressure distribution in said slice in accordance with an oxygen dissociation curve of the oxygen content indicator substance under a standard temperature and under a standard acidity;
   means for correcting respective data of the oxygen partial pressure distribution on the basis of differences between the temperature distribution and the standard temperature at respective data points of said slice and of differences between the acidity distribution and the standard acidity of the respective data points; and means for displaying the oxygen partial pressure distribution corrected with said correcting means as a picture image.

13. A living-body measuring apparatus according to claim 12, further comprising means for displaying the distribution of oxygen partial pressure distribution obtained by said converting means, in the slice of the living body, as a picture image.

14. A living-body measuring apparatus according to claim 13, further comprising means for displaying the temperature distribution in the slice of the living body as a picture image and means for displaying the acidity distribution in the predetermined slice of the living body as a picture image.

15. A living-body measuring apparatus according to claim 14, wherein displaying means displays a picture image showing the distribution of oxygen partial pressure distribution obtained by said converting means, a picture image showing temperature distribution, a picture image showing acidity distribution, and a picture image showing the distribution of oxygen partial pressure having been subjected to temperature correction and acidity correction all at the same time as a single display screen.

16. A living-body measuring method for measuring the oxygen partial pressure in a living body non-invasively, comprising the steps of:
 throwing light on a living body;
 detecting light having passed through the living body;
 obtaining the oxygen saturation of an oxygen content indicator substance at a predetermined portion of the living body, from the detected light;
 generating nuclear magnetic resonance in the living body, to obtain the temperature of the predetermined portion from a first resonance characteristic of the nuclear magnetic resonance;
 generating nuclear magnetic resonance in the living body, to obtain the acidity of the predetermined portion from a second resonance characteristic of the nuclear magnetic resonance;
 determining an oxygen partial pressure from the oxygen saturation in accordance with an oxygen dissociation curve of the oxygen content indicator which is compensated with the temperature and the acidity; and
 displaying the oxygen partial pressure.

17. A living-body measuring apparatus for measuring the oxygen partial pressure distribution in a slice of living body non-invasively, comprising:
 means for throwing light on a living body;
 means for detecting light having passed through the slice of the living body;
 means for obtaining the oxygen saturation distribution of an oxygen content indicator substance in the slice of living body, from the detected light;
 means for generating nuclear magnetic resonance in the slice of the living body, to obtain the temperature distribution in the slice from a first resonance characteristic of the nuclear magnetic resonance;
 means for generating nuclear magnetic resonance in the slice of the living body, to obtain the acidity distribution in the slice from a second resonance characteristic of the nuclear magnetic resonance;
 means for determining an oxygen partial pressure distribution in the slice from the oxygen saturation distribution in accordance with the oxygen dissociation curves of the oxygen content indicator substance which are compensated with the temperature distribution and the acidity distribution; and
 means for displaying the oxygen partial pressure distribution as a picture image.

* * * * *